US010959964B2

(12) United States Patent
Sauerland et al.

(10) Patent No.: US 10,959,964 B2
(45) Date of Patent: Mar. 30, 2021

(54) USE OF A SPRAYABLE COMPOSITION COMPRISING AMBROXOL

(75) Inventors: Sandra Sauerland, Ummendorf (DE); Julia Elisabeth Boni, Memmingen (DE); Bernd Karl Plohmann, Oberhoefen (DE)

(73) Assignee: SANOFI-AVENTIS DEUTSCHLAND GMBH, Paris (FR)

( * ) Notice: Subject to any disclaimer, the term of this patent is extended or adjusted under 35 U.S.C. 154(b) by 215 days.

(21) Appl. No.: 14/003,375

(22) PCT Filed: Mar. 13, 2012

(86) PCT No.: PCT/EP2012/054406
§ 371 (c)(1),
(2), (4) Date: Nov. 8, 2013

(87) PCT Pub. No.: WO2012/123466
PCT Pub. Date: Sep. 20, 2012

(65) Prior Publication Data
US 2014/0066518 A1     Mar. 6, 2014

(30) Foreign Application Priority Data

Mar. 14, 2011   (EP) ...................................... 1158043

(51) Int. Cl.
*A61K 31/137*  (2006.01)
*A61K 9/00*    (2006.01)

(52) U.S. Cl.
CPC ............ *A61K 31/137* (2013.01); *A61K 9/006* (2013.01); *A61K 9/0073* (2013.01)

(58) Field of Classification Search
CPC .................................................. A61K 31/137
See application file for complete search history.

(56) References Cited

U.S. PATENT DOCUMENTS

| 6,159,459 A * | 12/2000 | Hunter et al. ............. 424/78.08 |
| 2005/0075403 A1 | 4/2005 | Esperester et al. |
| 2005/0266058 A1* | 12/2005 | Esperester ........... A61K 31/137 424/448 |
| 2008/0319087 A1 | 12/2008 | Esperester et al. |

FOREIGN PATENT DOCUMENTS

| CN | 1695601 A   |   | 11/2005 |            |
| CN | 101606903   | * | 12/2009 | A61K 9/08  |
| CN | 101606903 A | * | 12/2009 | A61K 9/08  |
| CN | 101810604   | * | 12/2009 | A61K 31/137|
| CN | 101810604 A | * | 8/2010  | A61K 31/137|
| EP | 1543826 A1  |   | 6/2005  |            |
| EP | 1820493 A2  |   | 8/2007  |            |
| JP | 10259124    | * | 9/1998  | A61K 9/08  |
| JP | 10259124 A  | * | 9/1998  | A61K 9/08  |
| WO | 2007023072 A2 |   | 3/2007 |            |

OTHER PUBLICATIONS

Schipper et al., Saliva as research material: Biochemical, physicochemical and practical aspects, Archives of oral biology, 52, 1114-1135, 2007.*
Ishiura et al., Thromboxane antagonism and cough in chronic bronchitis, Annals of Medicine, 35, 135-139, 2003.*
International Search Report for PCT/EP2012/054406 filed on Mar. 13, 2012.
International Preliminary Report on Patentability for PCT/2012/05506, dated Sep. 17, 2013, 8 pages.
C. de Mey et al., "Efficacy and Safety of an Oral Ambroxol Spray in the Treatment of Acute Uncomplicated Sore Throat", DOI 10.1055/s-0035-1547229 Drug Res 2015; 65: 658-667, Dec. 15, 2014.
EP Search Report for European Patent Application No. 11158043, dated Sep. 6, 2011, 6 pages.

* cited by examiner

*Primary Examiner* — Kortney L. Klinkel
*Assistant Examiner* — Tori Strong
(74) *Attorney, Agent, or Firm* — Edell, Shapiro & Finnan, LLC

(57) ABSTRACT

The present invention relates to ambroxol hydrochloride for the treatment of acute pharyngitis, wherein ambroxol hydrochloride as a sprayable composition comprising up to 30 mg/ml ambroxol hydrochloride is administered locally in a dose of 1 to 20 mg.

5 Claims, No Drawings

USE OF A SPRAYABLE COMPOSITION COMPRISING AMBROXOL

FIELD OF THE INVENTION

Background to the Invention

Ambroxol hydrochloride (trans-4-[(2-amino-3,5-dibromobenzyl)amino]cyclohexanol hydrochloride) was originally developed as a mucoregulatory and secretolytic active substance, as pharmacological studies showed that it promotes the formation of secretions in the airways and increases ciliary activity. It was also found to exhibit a local anaesthetic activity.

Ambroxol in the form of lozenges (20 mg of active substance) is licensed for example under the brand names Mucoangin® and Lysopadol® for pain relief in acute sore throat, which is characteristic of acute pharyngitis.

Acute pharyngitis is an inflammatory syndrome of the pharynx and/or tonsils with various causes. Acute pharyngitis is characterised by rapid onset and a relatively short duration. Normally it is a benign, self-limiting disease that lasts no more than 2 to 4 days. Acute pharyngitis may be part of a general infection of the upper respiratory tract or may occur as a specific local infection of the pharynx. Most cases are caused by a virus infection and occur in connection with a viral infection or a cold. However, a number of other factors may also cause sore throat, such as for example toxins, allergies, trauma or dry air.

The treatment methods may be divided into treatment of the symptoms (analgesics, steroids, local anaesthetics) and treatment of the causes (antibiotics, virustatics). Symptomatic treatments aim to reduce the pain and illness, whereas causal treatments aim to cure the pharyngitis or try to prevent long-term complications such as rheumatic fever.

As there is no specific treatment for acute (viral) pharyngitis, these infections are treated by controlling the symptoms until the virus infection recedes. As the main symptom of pharyngitis is sore throat, the most important thing for the patient is to obtain relief from this. Consequently, locally administered and locally acting substances such as ambroxol hydrochloride are the means of choice for treating sore throats.

It has already been shown that treatment with ambroxol hydrochloride is well tolerated and effectively relieves the pain in patients suffering from acute pharyngitis. In spite of the exceptionally good tolerance of ambroxol lozenges, in some individual cases incompatibilities and side effects are theoretically possible.

The aim of the present invention was to provide alternative preparation forms for ambroxol hydrochloride which ensure that the known efficacy is achieved. If possible, the effect should be obtained with the same or, preferably, a lower dose of the active substance. The effect should if necessary set in rapidly, i.e. within less than 30 minutes. The effect should also last for a reasonably long time, i.e. for several hours, particularly more than 2 hours.

In this context EP 1 543 826 teaches that highly concentrated solutions of ambroxol hydrochloride (≥40 mg/ml), administered in the form of a mouthwash or spray, are required. However, the high concentration of ambroxol hydrochloride requires special measures to be taken in the preparation of the solutions because of its limited solubility.

SUMMARY OF THE INVENTION

Surprisingly it has now been found that sprayable compositions of ambroxol hydrochloride containing 1 to 30 mg/ml ambroxol hydrochloride are suitable for the treatment of acute pharyngitis if they are administered locally in a dose of 1 to 20 mg. This procedure ensures a high efficacy, a rapid onset of activity and high tolerance.

Consequently, the present invention relates to ambroxol hydrochloride for the treatment of acute pharyngitis, wherein ambroxol hydrochloride is administered locally in a dosage of 1 to 20 mg as a sprayable composition containing 1 to 30 mg/ml ambroxol hydrochloride.

DETAILED DESCRIPTION OF THE INVENTION

Within the scope of the present invention the term "administered locally" denotes the direct application of the active substance to the inflamed region in question. Within the scope of the present invention the term "dosage" denotes the locally administered amount of active substance. The dosage of ambroxol hydrochloride administered is preferably 2.5 to 10 mg, more particularly 2.5 mg, 5 mg or 10 mg, preferably 3 to 8 mg.

Usually, ambroxol hydrochloride will be applied to the affected inflamed region by means of a spray applicator. The active substance can thus be administered directly to the affected inflamed region without the tongue and other parts of the oral and pharyngeal cavity coming into contact with the active substance. Accordingly, in another aspect, the present invention relates to an applicator device for the local administration of 1 to 20 mg ambroxol hydrochloride, comprising a spray applicator and a container containing a sprayable composition containing 1 to 30 mg/ml ambroxol hydrochloride.

Usually, the spray applicator will be selected such that the dose of 1 to 20 mg is administered by a single or repeated actuation of the spray device.

It has proved particularly advantageous to select the spray applicator such that the dose of 1 to 20 mg is administered by an even number of actuations of the spray applicator, for example 2 or 4 actuations. This enables the intended dose to be administered uniformly to opposite sides of the oropharynx.

Preferably, the active substance will be administered as described above 1 to 10 times, most preferably up to 6 times, over the course of a day. Preferably a daily dose of ambroxol hydrochloride of 1 to 200 mg/day, particularly preferably 15 to 60 mg/day, will be administered.

In another aspect the present invention relates to the use of ambroxol hydrochloride for the treatment of acute pharyngitis, wherein ambroxol hydrochloride is administered locally in a dose of 1 to 20 mg as a sprayable composition containing 1 to 30 mg/ml ambroxol hydrochloride.

In another aspect the present invention relates to a method of treating acute pharyngitis, wherein ambroxol hydrochloride is administered locally in a dose of 1 to 20 mg as a sprayable composition containing 1 to 30 mg/ml ambroxol hydrochloride.

The sprayable compositions according to the present invention preferably contain water and ethanol as solvents. The proportion of water is usually higher than that of ethanol. The sprayable compositions usually have a water content of at least 50% by weight, preferably at least 60% by weight, particularly preferably at least 80% by weight and most particularly preferably at least 85% by weight, based in each case on the total weight of the composition.

Moreover, the sprayable compositions according to the invention preferably contain at least one surfactant, particularly a non-ionic surfactant, such as for example polyoxyethylene sorbitan monolaurate (polysorbate). The amount of surfactant is usually in the region of <1% by weight, particularly in the range from 0.05 to 0.5% by weight, based in each case on the total weight of the composition.

The sprayable compositions according to the invention are, in particular, aqueous compositions containing 1 to 30 mg/ml ambroxol hydrochloride, 50 to 200 mg/ml ethanol, 0.5 to 2 mg/ml of a surfactant and other additives selected from among pH-regulating substances, sweeteners, flavourings and/or preservatives.

In another aspect the present invention therefore relates to a sprayable aqueous composition for the treatment of acute pharyngitis, containing 1 to 30 mg/ml ambroxol hydrochloride, 50 to 200 mg/ml ethanol, 0.5 to 2 mg/ml of a surfactant and other additives selected from among pH-regulating substances, sweeteners, flavourings and/or preservatives. In a special embodiment the sprayable compositions used according to the invention consist of 1 to 30 mg/ml of ambroxol hydrochloride, 50 to 200 mg/ml of ethanol, 0.5 to 2 mg/ml of a surfactant and other additives selected from among pH-regulating substances, sweeteners, flavourings and/or preservatives.

The term "aqueous composition" in this context means that the composition according to the invention contains water as solvent.

The sprayable compositions according to the invention preferably contain 4 to 25 mg/ml ambroxol hydrochloride.

Usually, the sprayable compositions according to the invention have a viscosity in the range from 1.4 to 1.6 mPa*s.

Usually, the sprayable compositions according to the invention have a pH in the range from 5.2 to 5.8.

The administration of the ambroxol-containing compositions according to the invention leads to a rapid onset of the pain-relieving activity with a long-lasting effect.

The invention is hereinafter explained more fully by means of some non-restrictive Examples.

Examples

A. Compositions According to the Invention 30 ml aliquots of an aqueous solution containing 17.86 mg/ml (solution 1), 8.93 mg/ml (solution 2) or 4.46 mg/ml ambroxol hydrochloride (solution 3), ethanol (96%, 84.1 mg/ml), polysorbate 20 (1 mg/ml), citric acid monohydrate/disodium hydrogen phosphate dihydrate (2.8 mg/ml), flavourings (1.3 mg/ml), sucralose (0.8 mg/ml) and water were prepared by mixing the individual components. The solutions obtained were transferred into spray bottles made of brown glass.

B. Administration of the Compositions According to the Invention

The compositions according to the invention are administered by 4 spray jets of 140 µl each to the inflamed tissue of the oropharynx.

Solution 1: the resulting dose (560 µl) is 10 mg ambroxol hydrochloride

Solution 2: the resulting dose (560 µl) is 5 mg ambroxol hydrochloride

Solution 3: the resulting dose (560 µl) is 2.5 mg ambroxol hydrochloride

This administration is carried out up to 6 times a day.

The invention claimed is:

1. A method of treating acute pharyngitis, the method comprising:
administering a sprayable composition of ambroxol hydrochloride to a subject with an applicator device such that the sprayable composition is delivered uniformly and locally to only an inflamed region of the oropharynx of the subject without the tongue and other parts of the oral and pharyngeal cavity coming into contact with the sprayable composition, the sprayable composition comprising ambroxol hydrochloride in an amount of 17.86 mg/ml to 30 mg/ml, ethanol, a polysorbate in an amount from 0.05 to 0.5% by weight of the sprayable compostion, a pH-regulating substance to regulate the pH of the sprayable composition within a range of 5.2 to 5.8, a sweetener, and water in an amount of at least 85% by weight of the sprayable composition;
wherein two or four sprays from the applicator device provides a dosage of 10 mg ambroxol hydrochloride administered locally to the subject.

2. The method according to claim 1, wherein the sprayable composition has a viscosity in the range from 1.4 to 1.6 mPa*s.

3. A method of treating acute pharyngitis, the method comprising:
administering a sprayable composition of ambroxol hydrochloride to a subject with an applicator device such that the sprayable composition is delivered uniformly and locally to only an inflamed region of the oropharynx of the subject without the tongue and other parts of the oral and pharyngeal cavity coming into contact with the sprayable composition, the sprayable composition comprising ambroxol hydrochloride in an amount of 17.86 mg/ml, ethanol, a polysorbate in an amount from 0.05 to 0.5% by weight of the sprayable compostion, a pH-regulating substance to regulate the pH of the sprayable composition within a range of 5.2 to 5.8, a sweetener, and water in an amount of at least 85% by weight of the sprayable composition;
wherein two or four sprays from the spray applicator provides a dosage of 10 mg ambroxol hydrochloride, administered locally to the subject.

4. An applicator device comprising a spray applicator and a container containing a sprayable composition, wherein the sprayable composition consists of:
ambroxol hydrochloride in an amount of 17.86 mg/ml to 30 mg/ml;
ethanol;
a polysorbate in an amount from 0.05 to 0.5% by weight of the sprayable compostion;
a pH-regulating substance to regulate the pH of the sprayable composition within a range of 5.2 to 5.8;
a sweetener; and
water in an amount of at least 85% by weight of the sprayable composition;
wherein two or four sprays from the spray applicator provides a dosage of 10 mg ambroxol hydrochloride administered locally to the subject, and the sprayable composition is delivered by the applicator device uniformly and locally to only an inflamed region of the oropharynx of the subject without the tongue and other parts of the oral and pharyngeal cavity coming into contact with the sprayable composition.

5. The application device of claim 4, wherein the amount of ambroxol hydrochloride in the sprayable composition is 17.86 mg/ml.

* * * * *